United States Patent
Tao et al.

(10) Patent No.: US 10,702,421 B2
(45) Date of Patent: Jul. 7, 2020

(54) MEDICAL PRESSURE SOCK WITH IMPROVED ANKLE MEDIAL PRESSURE AND ANTIBACTERIAL FUNCTION

(71) Applicant: The Hong Kong Research Institute of Textiles and Apparel Limited, Hong Kong (HK)

(72) Inventors: Xiaoming Tao, Hong Kong (HK); Qiao Li, Hong Kong (HK); Yuheng Zhang, Hong Kong (HK); Sui Yee Lui, Hong Kong (HK); Cheuk-Wa Chad Tse, Hong Kong (HK)

(73) Assignee: The Hong Kong Research Institute of Textiles and Apparel Limited, Hong Kong (HK)

( * ) Notice: Subject to any disclaimer, the term of this patent is extended or adjusted under 35 U.S.C. 154(b) by 375 days.

(21) Appl. No.: 15/648,609

(22) Filed: Jul. 13, 2017

(65) Prior Publication Data
US 2018/0014978 A1    Jan. 18, 2018

(30) Foreign Application Priority Data
Jul. 13, 2016 (CN) .......................... 2016 1 0550526

(51) Int. Cl.
*A61F 13/08* (2006.01)
*A01N 25/34* (2006.01)
*A61F 13/06* (2006.01)

(52) U.S. Cl.
CPC .............. *A61F 13/08* (2013.01); *A01N 25/34* (2013.01); *A61F 13/066* (2013.01)

(58) Field of Classification Search
CPC ...... A61F 13/06; A61F 13/064; A61F 13/066; A61F 13/08
USPC ................................................ 602/60–62, 65
See application file for complete search history.

(56) References Cited

U.S. PATENT DOCUMENTS

| | | | | |
|---|---|---|---|---|
| 2009/0005717 | A1* | 1/2009 | Brzank | A61F 5/0111 602/65 |
| 2009/0053521 | A1* | 2/2009 | Goda | D01D 5/253 428/362 |
| 2010/0305535 | A1* | 12/2010 | Leeming | A61F 13/069 604/367 |
| 2017/0056233 | A1* | 3/2017 | Kelly | A61F 5/32 |

* cited by examiner

*Primary Examiner* — Keri J Nelson

(57) ABSTRACT

A medical pressure sock with an antibacterial fabric packing and an adhesive structure is provided. The antibacterial fabric packing is arranged on the inner surface. The adhesive structure is arranged at a position the pressure of which needs to be improved relative to the medial ankle of the lower limb; an adhesive surface connected with the adhesive structure is arranged on one side of the antibacterial fabric packing; the antibacterial fabric packing cross section includes a cross section front side, a cross section intermediate connection layer and a cross section rear side; the cross section intermediate connection layer has a special shape capable of being inserted into the cross section front side and the cross section rear side. The provided medical pressure sock solves the imbalance pressure and the not long-lasting antibacterial time problems of the traditional pressure socks, thus speeding up the recovery process of patients with varicose veins.

4 Claims, 3 Drawing Sheets antibacterial fabric packing 200 antibacterial pressure sock antibacterial fabric packing structure 400 adhesive surface of the antibacterial fabric packing 201 antibacterial fabric packing 200

MEDICAL PRESSURE SOCK WITH IMPROVED ANKLE MEDIAL PRESSURE AND ANTIBACTERIAL FUNCTION

CROSS REFERENCE TO RELATED APPLICATIONS

The present application claims the benefit of Chinese Patent Application No. 201610550526.6 filed on Jul. 13, 2016. All the above are hereby incorporated by reference.

TECHNICAL FIELD

The present application relates to the field of medical antibiotic pressure socks, and more particularly it relates to a medical pressure sock with improved ankle medial pressure and antibacterial function.

BACKGROUND OF THE INVENTION

The medical pressure sock is an important component in the treatment of varicose veins. It is therefore recommended that patients with varicose veins use pressure socks with a pressure of 10-50 mmHg at the ankles. At present, commercial products of pressure socks generally use high elastic pressure socks, which exert pressure on the legs, ankles and feet of patients. The pressure socks have the greatest pressure at the ankle and have a gradually smaller pressure at the knee and thighs. By compressing the superficial veins, arteries, and muscles, the circulation of blood passes through the narrow circulation channels, increasing arterial pressure and making blood return to the heart. The current pressure socks produce a bottom-up gradually decreasing pressure on limbs by the fabric structure containing the coil and the embedded yarn.

But the shape of the cross section of the human body lower limb cross section is irregular, from bottom to top, the shape of the cross section of the human body lower limb changes from an irregular shape to an oval. The irregular shape of the lower limb protrudes consists of three parts: the medial malleolus located inside the ankle, the external malleolus located outside the ankle, and the achilles tendon located behind the ankle. For the cross section of the upper part of the lower limb, there is not much difference between wearing socks and not wearing socks. But for the ankle the bone of which moves frequently, there is much difference between wearing socks and not wearing socks. This difference is caused by the prominent bones. When the tester wears traditional pressure socks, these prominent bones make the socks unable to contact with the concave parts surrounding the bones. But the ulcer associated with varicose veins often appears at the concave parts on the inside of the ankle. Therefore, the pressure of the traditional pressure socks on the concave parts on the inside of the ankle is not enough. Thus it cannot be applied to this field.

The traditional antibacterial fabric uses either chemicals or silver ions to achieve the antibacterial effect, and this has a negative impact on the health of consumers. The antibacterial effect of these methods is short. In the treatment of antibacterial fabric a number of antimicrobial drugs are also added, which will cause a certain degree of fiber and fabric contamination Or the cost of raw materials for traditional antibacterial fabrics is too high, which limits the use of antibacterial fabrics in medical pressure socks.

SUMMARY OF THE INVENTION

The present application combines pressure socks with new antibacterial materials and proposes a medical pressure sock with improved ankle medial pressure and antibacterial function. An antibacterial fabric packing is arranged on the inner surface of the antibacterial pressure sock and is configured to improve the pressure of the pressure sock on the medial ankle of the lower limb, an adhesive structure is arranged on the antibacterial pressure sock; the adhesive structure is arranged at a position the pressure of which needs to be improved relative to the medial ankle of the lower limb; an adhesive surface which can be connected with the adhesive structure of the pressure sock is arranged on one side of the antibacterial fabric packing;

the antibacterial fabric packing cross section includes a cross section front side, a cross section intermediate connection layer and a cross section rear side; the cross section intermediate connection layer has a special shape capable of being inserted into the cross section front side and the cross section rear side so that the cross section front side is connected to the cross section rear side.

The medical pressure sock with improved ankle medial pressure and antibacterial function according to the present application, the cross section front side constitutes the adhesive surface of the antibacterial fabric packing, the cross section rear side constitutes the other side of the antibacterial fabric packing, the cross section intermediate connection layer constitutes the middle part of the antibacterial fabric packing.

The medical pressure sock with improved ankle medial pressure and antibacterial function according to the present application, the medial ankle of the lower limb is a recessed portion around the medial malleolus.

The medical pressure sock with improved ankle medial pressure and antibacterial function according to the present application, the antibacterial fabric packing is connected with the adhesive structure of the antibacterial pressure sock, each position that needs increasing pressure on the antimicrobial pressure socks comprises at least one antibacterial fabric packing.

The medical pressure sock with improved ankle medial pressure and antibacterial function according to the present application, the antibacterial pressure sock and the antibacterial fabric packing are made of fabric that is made of blended fibers of a copolymer of antibacterial functional polylactic acid and poly 3-hydroxybutyrate-co-3-hydroxyvalerate.

THE BENEFICIAL EFFECT OF THE INVENTION

The traditional pressure socks with high elasticity compresses the superficial veins, arteries, and muscles to make the circulation of blood pass through the narrow circulation channels, thus increasing arterial pressure and making blood return to the heart. But the pressure imbalance caused by the protruding part of the lower limb ankle has been ignored. The ulcer will be produced around the prominent part of the lower limbs with a relatively small pressure and poor blood circulation, thus the lower part of the body, especially the foot, is more likely to produce bacteria. The present application combines pressure socks with new antibacterial materials and proposes a medical pressure sock with improved ankle medial pressure and antibacterial function to solve the imbalance pressure and the not long-lasting antibacterial time problems of the traditional pressure socks, thus speeding up the recovery process of patients with varicose veins.

BRIEF DESCRIPTION OF THE DRAWINGS

The present application will be further described below with reference to the accompanying drawings, in which.

EMBODIMENT OF THE INVENTION

Figure 1:
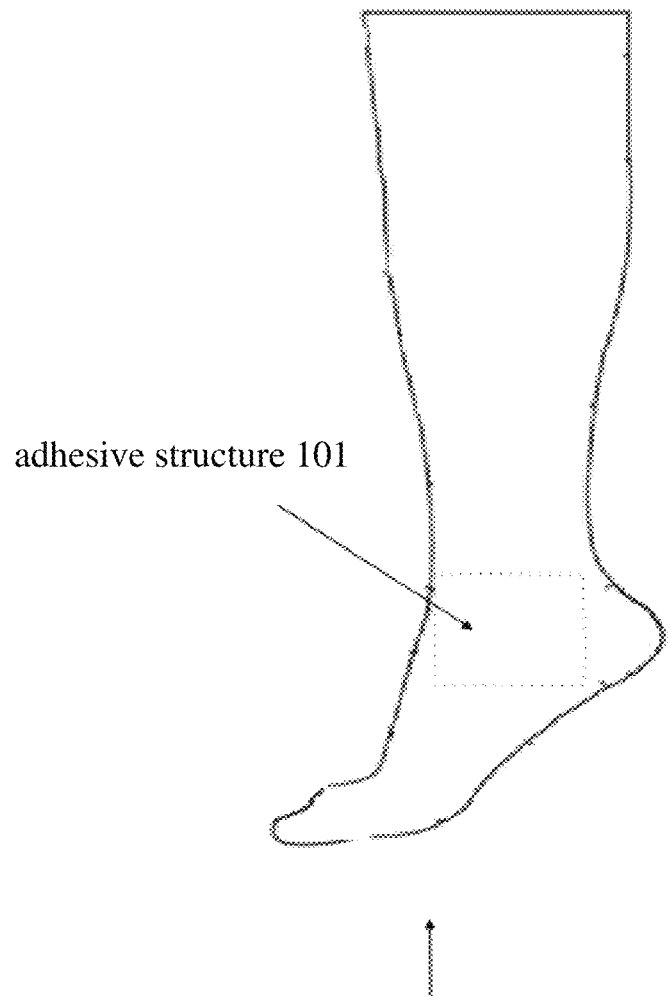
FIG. 1 is a schematic view of the medical pressure sock with improved ankle medial pressure and antibacterial function according to the present application.
Figure 2:
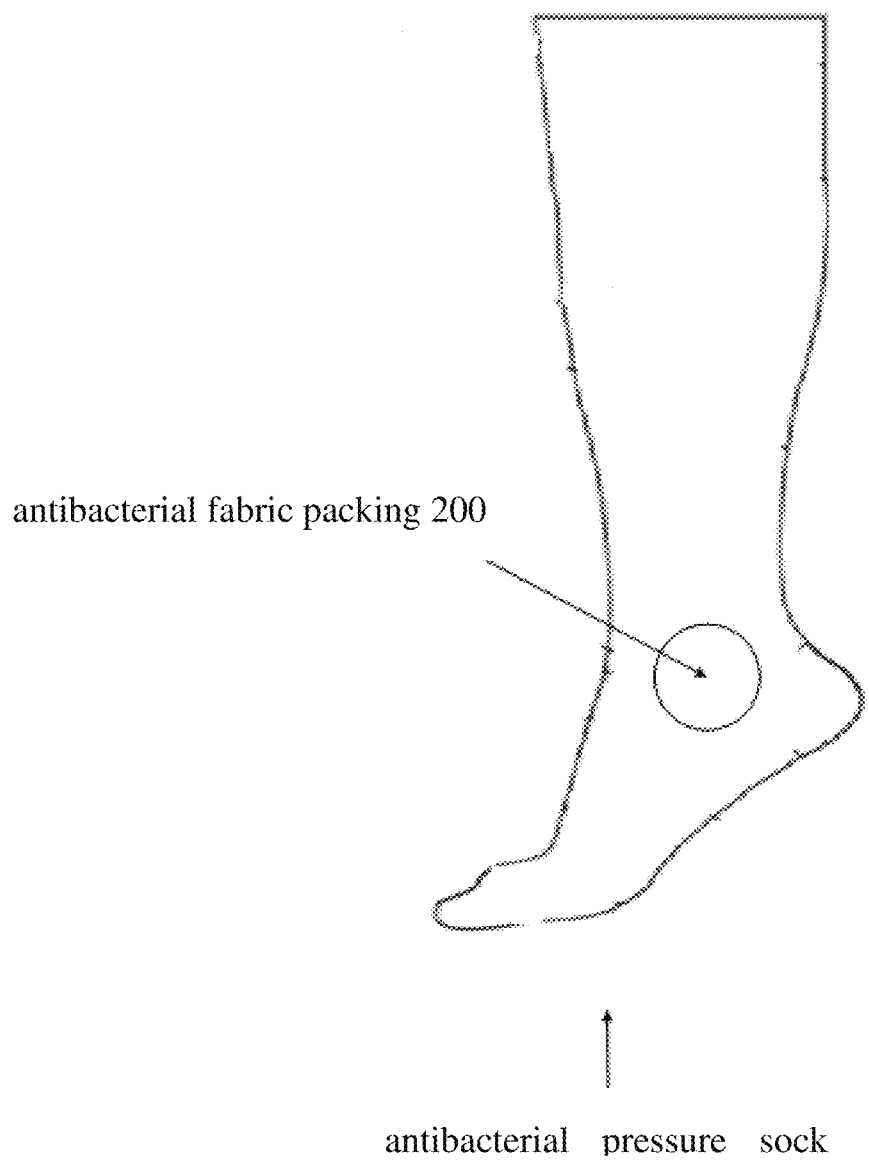
FIG. 2 is a schematic view of the medical pressure sock with improved ankle medial pressure and antibacterial function which is filled with antibacterial fabric packing according to the present application.

FIG. 1 is a schematic view of the antibacterial pressure sock 100 according to the present application; FIG. 2 is a schematic view of the antibacterial pressure sock 100 filled with antibacterial fabric packing 200 according to the present application; please refer to FIG. 1 and FIG. 2, the traditional pressure socks with high elasticity compresses the superficial veins, arteries, and muscles to make the circulation of blood pass through the narrow circulation channels, thus increasing arterial pressure and making blood return to the heart. But the pressure imbalance caused by the protruding part of the lower limb ankle has been ignored. The ulcer will be produced around the prominent part of the lower limbs with a relatively small pressure and poor blood circulation, thus the lower part of the body, especially the foot, is more likely to produce bacteria. A Medical antibacterial pressure sock 100 is proposed, an antibacterial fabric packing 200 is arranged on the inner surface of the antibacterial pressure sock 100 and is configured to improve the pressure of the pressure sock 100 on the medial ankle of the lower limb, an adhesive structure 101 is arranged on the antibacterial pressure sock 100; the adhesive structure 101 is arranged at a position the pressure of which needs to be improved relative to the medial ankle of the lower limb; an adhesive surface 201 which can be connected with the adhesive structure 101 of the pressure sock is arranged on one side of the antibacterial fabric packing 200. By filling the antibacterial fabric packing 200, the pressure of the pressure sock on the area around the medial malleolus of the lower limb ankle is balanced, promoting the blood circulation from the lower limbs to the heart. Meanwhile, the antibacterial fabric packing uses antibacterial materials, reducing the likelihood of infection of patients with varicose veins in the area around the lower limb ankle which is prone to ulcer, thus speeding up the recovery process of patients with varicose veins.

Figure 3:
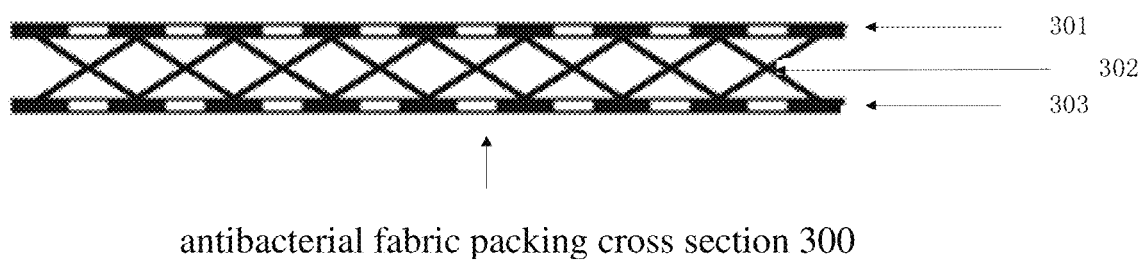
FIG. 3 is a schematic view of the antibacterial fabric packing cross section according to the present application.

FIG. 3 is a schematic view of the antibacterial fabric packing cross section 300 according to the present application; please refer to FIG. 3, the antibacterial fabric packing cross section 300 includes three parts: a cross section front side 301, a cross section intermediate connection layer 302 and a cross section rear side 303; the cross section front side 301 constitutes the adhesive surface; the cross section rear side 303 constitutes the other side of the antibacterial fabric packing; the cross section intermediate connection layer 302 has a special physical structure, such as a clover structure, capable of being inserted into the cross section front side 301 and the cross section rear side 303 of the fabric so that the cross section front side 301 is connected to the cross section rear side 303; and the cross section intermediate connection layer 302 also has the function of dredging water.

Figure 4:
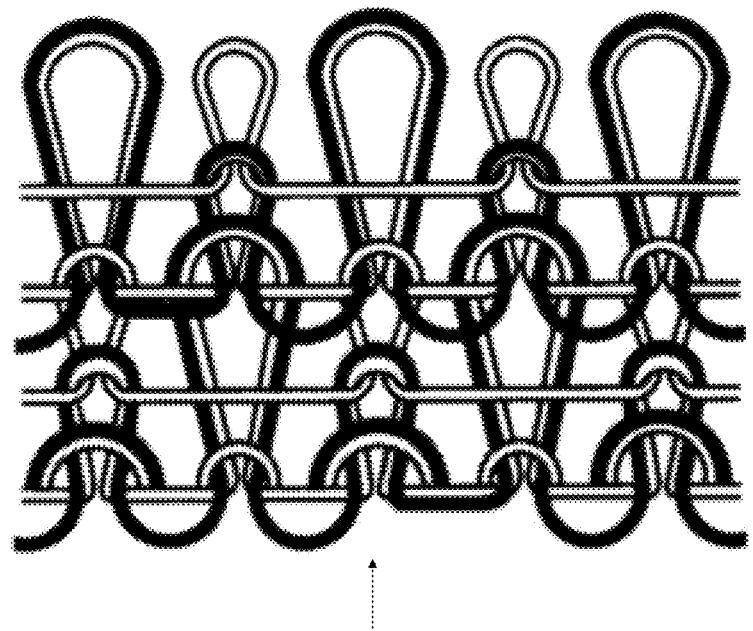
FIG. 4 is a schematic view of the antibacterial fabric packing according to the present application.
Figure 5:
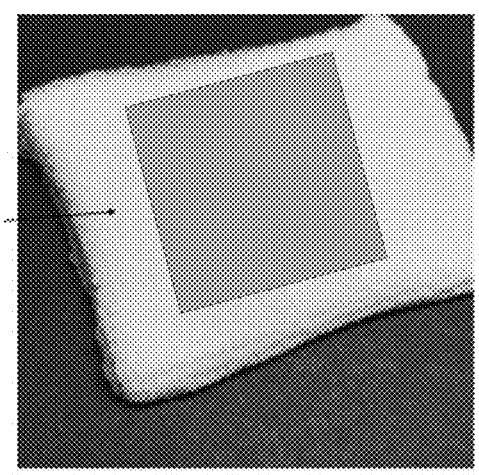
FIG. 5 is a schematic view of the side of the antibacterial fabric packing with adhesive surface according to the present application.

As shown in FIG. 2, the amount of the antibacterial fabric packing 200 can be determined according to the patient's needs. At least one antibacterial fabric packing 200 is added at the lower limb part whose pressure from the pressure sock is needed to be balanced. If the blood circulation is not good, the amount of the antibacterial fabric packing can be increased until the pressure of the pressure sock is balanced to an appropriate level. FIG. 4 is a schematic view of the antibacterial fabric packing 200 according to the present application; FIG. 5 is a schematic view of the side of the antibacterial fabric packing 200 with adhesive surface according to the present application; please refer to FIG. 4 and FIG. 5, the structure of antibacterial fabric packing 200 adopts a fluffy and thick fabric structure 400 and has a soft feeling. One side of the antibacterial fabric packing 200 is provided with an adhesive surface 201 so as to be securely connected to the pressure sock 100. Thus, even if the lower limb is moving, the antibacterial fabric packing can still play the role of increasing the pressure at the relevant position without displacement.

The antibacterial pressure sock 100 is a high elastic pressure sock, which can effectively increase the pressure in the relevant position when filled with the antibacterial fabric packing 200 to achieve the purpose of promoting blood circulation. The antibacterial pressure sock 100 and the antibacterial fabric packing 200 are made of fabric that is made of blended fibers of a copolymer of antibacterial functional polylactic acid and poly 3-hydroxybutyrate-co-3-hydroxyvalerate, and do not contain any antibacterial and metal ions. It has the advantages of low cost, easy manufacture and long lasting antibacterial effect and is more easily to be widely used in the medical field.

While the embodiments of the present invention are described above, it should be understood that it is intended to be exemplary not to be limiting of the present invention. In the inspiration of the present invention, those ordinary skills in the art can also make many modifications without breaking away from the subject of the present invention and the protection scope of the claims. All these modifications belong to the protection of the present invention. Accordingly, the scope of protection of the present invention is limited only to the embodiments described above, but should be defined in accordance with the claims and their equivalents.

The invention claimed is:

1. A medical pressure sock (100) with increased ankle medial pressure and antibacterial function, wherein, an antibacterial fabric packing (200) is arranged on an inner surface of the medical pressure sock (100) and is configured to increase the pressure of the medical pressure sock (100) on a medial ankle of a lower limb, the medial ankle of the lower limb is a recessed portion around the medial malleolus, an adhesive structure (101) is arranged on the medical pressure sock (100); the adhesive structure (101) is arranged at a position the pressure of which needs to be increased relative to the medial ankle of the lower limb; the antibacterial fabric packing (200) is connected with the adhesive structure (101) of the medical pressure sock; an adhesive surface (201) which can be connected with the adhesive structure (101) of the pressure sock is arranged on one side of the antibacterial fabric packing (200);

a cross section of the antibacterial fabric packing (300) includes a cross section front side (301), a cross section intermediate connection layer (302) and a cross section rear side (303); the cross section intermediate connection layer (302) has a shape capable of being inserted into the cross section front side (301) and the cross section rear side (303) so that the cross section front side (301) is connected to the cross section rear side (303).

2. The medical pressure sock (100) with increased ankle medial pressure and antibacterial function according to claim 1, wherein, the cross section front side (301) constitutes the adhesive surface (201) of the antibacterial fabric packing, the cross section rear side (303) constitutes the other side of the antibacterial fabric packing (200), the cross section intermediate connection layer (302) constitutes the middle part of the antibacterial fabric packing (200).

3. The medical pressure sock (100) with increased ankle medial pressure and antibacterial function according to claim 1, each position that needs increasing pressure on the medical pressure socks (100) comprises at least one antibacterial fabric packing (200).

4. The medical pressure sock (100) with increased ankle medial pressure and antibacterial function according to claim 1, wherein, the medical pressure sock (100) and the antibacterial fabric packing (200) are made of fabric that is made of blended fibers of a copolymer of antibacterial functional polylactic acid and poly 3-hydroxybutyrate-co-3-hydroxyvalerate.

\* \* \* \* \*